(12) United States Patent
McGregor et al.

(10) Patent No.: US 9,000,254 B2
(45) Date of Patent: Apr. 7, 2015

(54) DISPOSABLE DIAPER WITH REDUCED BULK

(75) Inventors: Judit Ester McGregor, Pet Lancy (CH); Nicole Anja Reichardt, Sulzbach Am Taunus (DE)

(73) Assignee: The Procter & Gamble Company, Cincinnati, OH (US)

(*) Notice: Subject to any disclaimer, the term of this patent is extended or adjusted under 35 U.S.C. 154(b) by 719 days.

(21) Appl. No.: 13/168,548

(22) Filed: Jun. 24, 2011

(65) Prior Publication Data
US 2012/0165776 A1   Jun. 28, 2012

(30) Foreign Application Priority Data
Jun. 25, 2010   (EP) .................................... 10167333

(51) Int. Cl.
| A61F 13/15 | (2006.01) |
| A61L 15/22 | (2006.01) |
| A61F 13/537 | (2006.01) |
| A61F 13/513 | (2006.01) |
| A61F 13/511 | (2006.01) |
| A61F 13/514 | (2006.01) |
| A61L 15/58 | (2006.01) |

(Continued)

(52) U.S. Cl.
CPC ..... *A61L 15/22* (2013.01); *A61F 2013/530481* (2013.01); *A61F 2013/8497* (2013.01); *A61F 13/537* (2013.01); *A61F 2013/53051* (2013.01); *A61F 13/51394* (2013.01); *A61F 2013/530518* (2013.01); *A61F 13/511* (2013.01); *A61F 13/51496* (2013.01); *A61F 13/84* (2013.01); *A61L 15/58* (2013.01)

(58) Field of Classification Search
CPC . A61F 13/42; A61F 13/511; A61F 13/51104; A61F 13/51394; A61F 13/51113; A61F 13/537; A61F 2013/8497; A61F 2013/422; A61F 2013/429; A61F 2013/51078; A61F 2013/530481; A61F 2013/53051; A61F 2013/530518; A61F 2013/530525; A61F 2013/5315; A61F 2013/53765
USPC .......................................................... 604/372
See application file for complete search history.

(56) References Cited

U.S. PATENT DOCUMENTS 5,352,217 A * 10/1994 Curro ............................ 604/378
H1575 H * 8/1996 Daugherty et al. ........... 428/138

(Continued)

FOREIGN PATENT DOCUMENTS

| EP | 1 301 156 B1 | 8/2006 |
| WO | WO 00/24351 A1 | 5/2000 |

(Continued)

OTHER PUBLICATIONS

PCT International Search Report, PCT/US2011/041811 date of mailing Aug. 2, 2011.

(Continued)

*Primary Examiner* — Lynne Anderson
(74) *Attorney, Agent, or Firm* — Andrew A Paul; Richard L. Alexander; Charles R. Ware (57) ABSTRACT

A disposable diaper is disclosed having reduced bulk, especially in the back waist region. Due to an opaque topsheet and a backsheet having a relatively high percentage of printed surface area, the diaper has reduced see-through even in those areas of the back waist region where no absorbent core is comprised.

18 Claims, 1 Drawing Sheet (51) Int. Cl.
*A61F 13/53* (2006.01)
*A61F 13/84* (2006.01)

(56) References Cited

U.S. PATENT DOCUMENTS

| | | | |
|---|---|---|---|
| 5,693,037 | A | 12/1997 | Lee et al. |
| 5,873,868 | A | 2/1999 | Nakahata |
| 6,262,331 | B1 | 7/2001 | Nakahata et al. |
| 7,824,385 | B2 | 11/2010 | Ecker et al. |
| 8,016,803 | B2 | 9/2011 | Mueller et al. |
| 8,344,202 | B2 * | 1/2013 | Schneider et al. ............ 604/367 |
| 2004/0122398 | A1 | 6/2004 | Schnabel et al. |
| 2005/0177120 | A1 * | 8/2005 | Olson et al. ................... 604/361 |
| 2007/0087169 | A1 | 4/2007 | McFall |
| 2008/0044616 | A1 * | 2/2008 | Hanao et al. .................... 428/68 |
| 2008/0108967 | A1 | 5/2008 | Mizushima et al. |

FOREIGN PATENT DOCUMENTS

| | | | |
|---|---|---|---|
| WO | WO 00-76442 | A1 | 12/2000 |
| WO | WO 02-07662 | A1 | 1/2002 |
| WO | WO 03-032884 | A1 | 4/2003 |
| WO | WO 2008-155722 | A1 | 12/2008 |

OTHER PUBLICATIONS

EP 2399557—Annex 1 of Brief in support of Notice of Opposition filed Apr. 11, 2014 (1 page).
EP 2399557—Annex 2 of Brief in support of Notice of Opposition filed Apr. 11, 2014 (1 page).
EP 2399557—Annex 3 of Brief in support of Notice of Opposition filed Apr. 11, 2014 (14 pages).
EP 2399557—Annex 4 of Brief in support of Notice of Opposition filed Apr. 11, 2014 (1 page).
EP 2399557—Brief in support of Notice of Opposition filed Apr. 11, 2014 (14 pages).
EP 2399557—Notice of Opposition filed Apr. 11, 2014 (5 pages).

\* cited by examiner

DISPOSABLE DIAPER WITH REDUCED BULK

FIELD

The present disclosure refers to disposable diapers which are comfortable due to reduced bulk. Moreover, the diapers look appealing to consumers and show good performance.

BACKGROUND

Today disposable absorbent articles, such as disposable diapers, are widely used. However, many disposable diapers are still relatively bulky which may result in reduced wearer comfort. Moreover, disposable diapers are sometimes hard to afford for consumers, especially in low income markets. Hence, there is still a need for disposable diapers, which are comfortable, have reduced bulk and can be manufactured at low cost.

SUMMARY

The present disclosure refers to a disposable diaper comprising a chassis and an absorbent core. The chassis comprises a topsheet and a backsheet. The absorbent core is disposed between the topsheet and backsheet.

The chassis has a longitudinal dimension and a chassis back waist region, a chassis back waist edge, a chassis front waist region and a chassis crotch region.

The chassis back waist region makes up 25% of the longitudinal dimension of the chassis beginning at the chassis back waist edge and extending towards the chassis crotch region.

The absorbent core has a longitudinal dimension co-extending with the longitudinal dimension of the chassis, the absorbent core having an absorbent core back waist region, an absorbent core back waist edge, an absorbent core front waist region and an absorbent core crotch region.

The absorbent core back waist edge is longitudinally offset by at least 10 percent from the chassis back waist edge, the 10% offset being based on the longitudinal dimension of the chassis.

The backsheet has a percentage of printed surface area of at least 14% in the chassis back waist region, and the topsheet has an opacity of at least 15%.

BRIEF DESCRIPTION OF THE DRAWINGS

These and other features, aspects and advantages of the present disclosure will become better understood with regard to the following description, appended claims, and accompanying FIG. 1, which is a plan view of a diaper of the present disclosure.

DETAILED DESCRIPTION

Definitions

"Absorbent article" refers to devices that absorb and contain body exudates, and, more specifically, refers to devices that are placed against or in proximity to the body of the wearer to absorb and contain the various exudates discharged from the body. Absorbent articles may include diapers, pants, training pants, adult incontinence undergarments, sanitary napkin, and the like. As used herein, the term "body fluids" or "body exudates" includes, but is not limited to, urine, blood, vaginal discharges, breast milk, sweat and fecal matter. Absorbent articles of the present disclosure include diapers, pants, training pants and/or sanitary napkins.

"Absorbent core" means a structure disposed between a topsheet and a backsheet of an absorbent article, such as a disposable diaper, for absorbing and containing liquid received by the absorbent article. For the present disclosure, the absorbent core does not include the topsheet, the backsheet and (if present) the acquisition system of the absorbent article.

"Absorbent material" means any material comprised by the absorbent core which is able to absorb liquid. For the present disclosure, the absorbent material may be selected from the group consisting of cellulose fibers, modified cellulose fibers (e.g. cross-linked cellulose fibers), particulate absorbent polymer material, absorbent foams, tissue, and combinations thereof. Substrate layers and any thermoplastic material of the absorbent core that may be used to immobilize the absorbent material are typically no absorbent materials.

"Comprise," "comprising," and "comprises" are open ended terms, each specifies the presence of what follows, e.g., a component, but does not preclude the presence of other features, e.g., elements, steps, components known in the art, or disclosed herein.

"Extensible" as used herein refers to an element or material which, upon application of a force, elongates beyond its original length by at least 10% if subjected to the following test: A rectangular piece of material or a rectangular piece of the element having a width of 2.54 cm and a length of 25.4 cm is maintained in a vertical position by holding the piece along its upper 2.54 cm wide edge along its complete width. A force of 10 N is applied onto the opposite lower edge along the complete width of the material for 1 minute at 25° C. Immediately after one minute, the length of the piece is measured while the force is still applied and the degree of elongation is calculated by subtracting the initial length (25.4 cm) from the length measured after one minute.

"Non-extensible" as used herein refers to an element or material which, upon application of a force as described above with respect to "extensible" elongates by no more than 10% beyond its original length. For the present disclosure, a non-extensible material or element is also considered to be non-elastic.

"Non-elastic" as used herein refers to an element or material which is non-extensible. Further, "non-elastic" also refers to an extensible element or material if the element or material does not recover by more than 20% if subjected to the following test, which is to be carried out immediately subsequent to the test on "extensibility" set out above: Immediately after the length of the rectangular piece of material/element has been measured while the 10N force is still applied, the force is removed and the piece is laid down flat on a table for 5 minutes (at 25° C.) to be able to recover. Immediately after 5 minutes, the length of the piece is measured again and the degree of elongation is calculated by subtracting the initial length (10 inch) from the length after 5 minutes. The elongation after one minute while the force has been applied (as measured with respect to "extensibility") is compared to the elongation after the piece has been laid down flat on a table for 5 minutes: If the elongation does not recover by more than 20%, the material or element is considered to be "non-elastic".

"Disposable" is used in its ordinary sense to mean an article that is disposed or discarded after a limited number of usage events over varying lengths of time, for example, less than about 20 events, less than about 10 events, less than about 5 events, or less than about 2 events. A disposable diaper is most often disposed after single use.

"Diaper" refers to an absorbent article generally worn by infants and incontinent persons about the lower torso so as to encircle the waist and legs of the wearer and that is specifically adapted to receive and contain urinary and fecal waste. As used herein, the term "diaper" also includes "pants" which is defined below.

A "nonwoven web" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter ($g/m^2$).

"Pant" or "training pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants".

"Particulate absorbent polymer material" as used herein refer to absorbent material which are cross linked polymeric materials that can absorb at least 5 times their weight of an aqueous 0.9% saline solution as measured using the Centrifuge Retention Capacity test (Edana 441.2-01). The particulate absorbent polymer material is in particulate form so as to be flowable in the dry state. In one embodiment of the present disclosure, a particulate absorbent polymer material is made of poly(meth)acrylic acid polymers. However, e.g. starch-based particulate absorbent polymer material is also comprised within the scope of the present disclosure. In various embodiments of the present disclosure, the absorbent core may comprise more than 80% of particulate absorbent polymer material by weight of absorbent material, more than 90% and more than 95% and even more than 98%. The absorbent material of the absorbent core may also consist solely of particulate absorbent polymer material. In one embodiment, the absorbent material may comprise less than 10% of cellulose fibers by weight of the absorbent material or may even be substantially cellulose free (i.e. less than 1% cellulose).

Disposable Diaper

Figure 1:
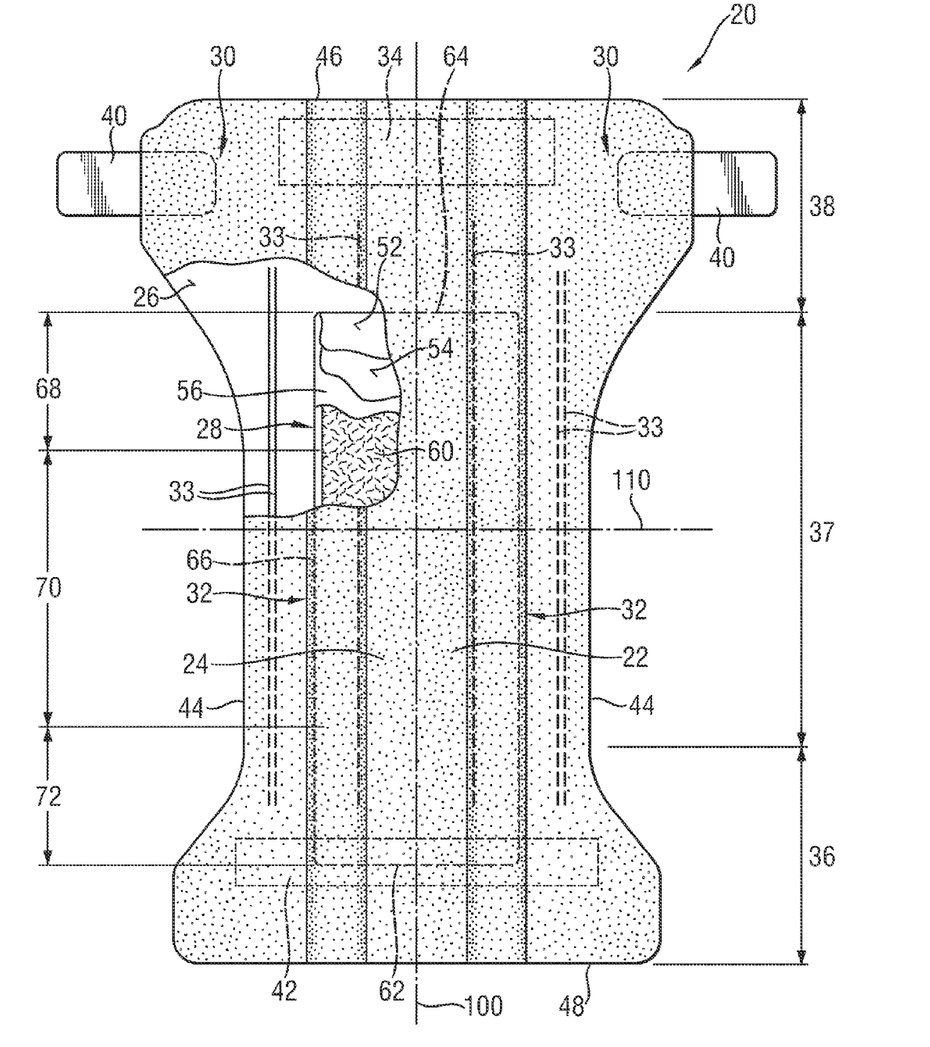

FIG. 1 is a plan view of a disposable diaper 20 according to an embodiment of the present disclosure. The disposable diaper 20 is shown in its flat out, uncontracted state (i.e. without elastic induced contraction) and portions of the disposable diaper 20 are cut away to more clearly show the underlying structure of the disposable diaper 20. A portion of the disposable diaper 20 that contacts a wearer is facing the viewer in FIG. 1. The disposable diaper 20 generally comprises a chassis 22 and an absorbent core 28 disposed in the chassis.

The chassis 22 of the disposable diaper 20 in FIG. 1 comprises the main body of the disposable diaper 20. The chassis 22 comprises an outer covering including a topsheet 24, which may be liquid pervious, and a backsheet 26, which may be liquid impervious. The absorbent core 28 is encased between the topsheet 24 and the backsheet 26. The chassis 22 may also include side panels 30, elasticized leg cuffs 32, and an elastic waist feature 34. The leg cuffs 32 and the elastic waist feature 34 may each typically comprise elastic members 33.

One end portion of the disposable diaper 20 is configured as the chassis front waist region 36 of the disposable diaper 20. The opposite end portion of the disposable diaper 20 is configured as the chassis back waist region 38 of the disposable diaper 20. The intermediate portion of the disposable diaper 20 is configured as the chassis crotch region 37, which extends longitudinally between the chassis front and back waist regions 36 and 38. The chassis crotch region 37 is that portion of the disposable diaper 20 which, when the disposable diaper 20 is worn, is generally positioned between the wearer's legs.

The disposable diaper 20 is depicted in FIG. 1 with its longitudinal axis 100 and its transverse axis 110. The periphery of the disposable diaper 20 is defined by the outer chassis edges of the disposable diaper 20 in which the longitudinal chassis edges 44 run generally parallel to the longitudinal axis 100 of the disposable diaper 20 and the chassis front and back waist edges 48 and 46 run between the longitudinal edges 44 generally parallel to the transverse axis 110 of the disposable diaper 20.

The longitudinal dimension of the chassis 22 extends along the longitudinal axis 100 from the chassis back waist edge 46 to the chassis front waist edge 48. The chassis 22 also has a transverse dimension extending along the transverse axis 110, which runs perpendicular to the longitudinal axis 100.

For embodiments, wherein the chassis back waist edge and/or the chassis front waist edge 46, 48 is/are not configured as a straight line extending in parallel to the transverse axis 110 of the chassis 22, the longitudinal dimension of the chassis 22 is determined along the longitudinal axis 100 by starting from the point of that chassis back waist edge 46 which is closest to the transverse axis 110 and terminating at the point of chassis front back edge 48 which is closest to the transverse axis 110.

In embodiments, wherein the topsheet 24 and/or the backsheet 26 are elastically extensible, the longitudinal dimension is determined while the topsheet and/or backsheet are in their relaxed, contracted state.

The chassis back and front waist edges 46 and 48 are comprised by the topsheet 24 and the backsheet 26. In one embodiment of the disclosure, the topsheet 24 and the backsheet 26 have the same longitudinal dimension and are coextensive. In embodiments, wherein the topsheet 24 and the backsheet 26 have different longitudinal dimensions, the front and back waist edges are defined by the component (i.e. the topsheet 24 or the backsheet 26) which extends longitudinally outward beyond the respective other component (i.e. the topsheet 24 or the backsheet 26). For the present disclosure, chassis features other than the topsheet 24 and backsheet 26 are not considered when determining the longitudinal dimension of the chassis.

The chassis front waist region 36 extends from the crotch region 37 to the chassis front waist edge 48 and makes up 25% of the longitudinal dimension of the chassis 22. The chassis back waist region 38 extends from the chassis crotch region 37 to the chassis back waist edge 46 and makes up 25% of the longitudinal dimension of the chassis 22. The chassis crotch region 37 makes up 50% of the longitudinal dimension of the chassis 22.

In order to keep the disposable diaper 20 in place about the wearer, at least a portion of the chassis back waist region 38 may be attached by the fastening member 40 to at least a portion of the chassis front waist region 36 to form leg opening(s) and an article waist. According to certain embodiments, the disposable diaper 20 may be provided with a re-closable fastening system joined to the chassis for securing the disposable diaper to a wearer, or may alternatively be provided in the form of a pant-type disposable diaper. The fastening system may include at least one fastening member 40 and at least one landing zone 42. In a pant-type disposable diaper, the article may comprise at least two side panels joined to the backsheet 26 and/or topsheet 24 along their longitudinal edges facing towards the longitudinal axis 100 and joined to each other along their longitudinal edges facing away from the longitudinal axis 100 to form a pant.

Taking a cross section of FIG. 1 along the transverse axis 110 and starting from the wearer facing side, the disposable diaper 20 comprises the topsheet 24, the absorbent core 28, and the backsheet 26. Disposable diaper 20 may also comprise an acquisition system 50 disposed between the topsheet 24 and the wearer facing side of the absorbent core 28. The acquisition system 50 may be in direct contact with the absorbent core 28.

The backsheet 26 may prevent the exudates absorbed by the absorbent core 28 and contained within the diaper 20 from soiling other external articles that may contact the diaper 20, such as bed sheets and undergarments. In certain embodiments, the backsheet 26 may be substantially impervious to liquids (e.g., urine) and comprise a laminate of a nonwoven and a thin plastic film such as a thermoplastic film having a thickness of 0.012 mm to 0.051 mm. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing liquid exudates from passing through the backsheet 20.

The backsheet 26, or any portion thereof, may be elastically extensible in one or more directions. In one embodiment, the backsheet 26 may comprise a structural elastic-like film ("SELF") web. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the disposable diaper 20 by any attachment means known in the art. For example, the attachment means may include a uniform continuous layer of adhesive, a patterned layer of adhesive, or an array of separate lines, spirals, or spots of adhesive. Alternatively, the attachment means may comprise heat bonds, pressure bonds, ultrasonic bonds, dynamic mechanical bonds, or any other suitable attachment means or combinations of these attachment means as are known in the art.

The topsheet 24 is positioned adjacent body surface of the absorbent core 28 and may be joined thereto and/or to the backsheet 26 by any attachment means known in the art. Suitable attachment means are described above with respect to means for joining the backsheet 26 to other elements of the disposable diaper 20. In one embodiment of the present disclosure, the topsheet 24 and the backsheet 26 are joined directly to each other in some locations and are indirectly joined together in other locations by directly joining them to one or more other elements of the disposable diaper 20.

The topsheet 24 is compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art.

In various embodiments of the present disclosure, at least a portion of the topsheet 24 is made of a hydrophobic material or is treated to be hydrophobic in order to isolate the wearer's skin from liquids contained in the absorbent core 28. If the topsheet 24 is made of a hydrophobic material, at least a portion of the upper surface of the topsheet 24 can be treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and/or immersing the material into the surfactant. Any portion of the topsheet 24 may be coated with a lotion as is known in the art.

Further, the topsheet 24 may be fully or partially extensible or elastic or may be foreshortened so as to provide a void space between the topsheet 24 and the core 28.

In various embodiments of the present disclosure, the topsheet 24 and/or the backsheet 26 are non-elastic. The topsheet 24 and/or the backsheet 26 may also be non-extensible.

The absorbent core 28 may comprise any absorbent material 60 which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.).

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures).

The periphery of the absorbent core 28 is defined by the outer absorbent core edges wherein the absorbent core front and back waist edges 62 and 64 run between the longitudinal edges 66 generally parallel to the transverse axis 110 of the disposable diaper 20.

The longitudinal dimension of the absorbent core 28 extends along the longitudinal axis 100 from the absorbent core front waist edge 62 to the absorbent core back waist edge 64. The absorbent core 28 also as a transverse dimension extending along the transverse axis 110, which is running perpendicular to the longitudinal axis 100.

The absorbent core has an absorbent core crotch region 70, an absorbent core front waist region 72 which extends from the absorbent core crotch region 70 to the absorbent core front waist edge 62 and makes up 25% of the longitudinal dimension of the absorbent core 28. The absorbent core back waist region 68 extends from the absorbent core crotch region 70 to the absorbent core back waist edge 64 and makes up 25% of the longitudinal dimension of the absorbent core 28. The absorbent core crotch region 70 makes up 50% of the longitudinal dimension of the absorbent core 28.

For embodiments, wherein the absorbent core front waist edge and/or the absorbent core back waist edge 62, 64 is/are not configured as a straight line extending in parallel to the transverse axis 110, the longitudinal dimension of the absorbent core 28 is determined along the longitudinal axis 100 by starting from the point of the absorbent core back waist edge 64 which is closest to the transverse axis 110 and terminating at the point of absorbent core front back edge 62 which is closest to the transverse axis 110.

In embodiments, wherein the absorbent core 28 comprises more than one layer, the longitudinal dimension of the absorbent core 28 is defined by the layer having the largest longitudinal dimension. This layer also defines the absorbent core front and back waist edges 62 and 64.

In various embodiments of the present disclosure, the absorbent core 28 is non-elastic. The absorbent core 28 may also be non-extensible.

According to the present disclosure, the absorbent core back waist edge 64 is longitudinally offset by at least 10% from the chassis back waist edge 46, as it has been found that the absorbent core is hardly made use of in that area of the disposable diaper. The 10% are determined based on the longitudinal extension of the chassis 22. In various embodiments of the present disclosure, the absorbent core back waist edge 64 is longitudinally offset by at least 12% from the chassis back waist edge 46, or even by at least 15%.

The absorbent core 28 typically comprises absorbent material 60 such as cellulose fibers, modified cellulose fibers, particulate absorbent polymer material, absorbent foams, tissue, or mixtures thereof. The absorbent core may comprise one or more substrates, particulate absorbent polymer material disposed on the one or more substrates and a thermoplastic composition one the particulate absorbent polymer material and at least a portion of the one or more of the substrates for immobilizing the particulate absorbent polymer material on the one or more substrates.

The one or more substrates may comprise or consist of nonwoven webs. The nonwoven webs will at least partially surround the particulate absorbent polymer material and the thermoplastic composition and these nonwoven webs are therefore often referred to as core wrap or core cover. The core wrap or core cover may consist of a first, upper nonwoven web 56 towards the body-facing surface of the absorbent article and of a second, lower nonwoven web 58 towards the garment-facing surface of the absorbent article. The first and second nonwoven webs 56, 58 may be continuously or intermittently bonded to each other around their perimeters. The first and second nonwoven webs 56, 58 may be made of the same nonwoven webs or may be made of different nonwoven webs, i.e. the first, upper nonwoven web 56 may be fluid pervious whereas the second, lower nonwoven web 58 may be fluid impervious. The core wrap/core cover may also consist of a single nonwoven web, which envelops the particulate absorbent polymer material and the thermoplastic composition. In a multilayer absorbent core, one or more layers of a substrate (e.g. a nonwoven web) may additionally be placed within the absorbent core to at least partially separate and segment the particulate absorbent polymer material.

In one embodiment of the absorbent core 28, the absorbent material 60 (e.g. the particulate absorbent polymer material) is distributed unevenly along the longitudinal dimension of the absorbent core 28. For example, the absorbent core crotch region 70 may comprise a higher amount of absorbent material 60 per area compared to the absorbent core front and back waist regions 72 and 68. In one embodiment, the absorbent core back waist region 68 comprises not more than 0.01 gram of absorbent material per $cm^2$ surface area (i.e. from 0 g of absorbent material per $cm^2$ to 0.01 gram per $cm^2$). In those embodiments, the absorbent core front waist region 72 can comprise at least 0.03 gram of absorbent material per $cm^2$, or even at least 0.04 gram per $cm^2$. The absorbent core crotch region 70 can comprise at least 0.04 gram of absorbent material per $cm^2$, or even at least 0.05 gram per $cm^2$. The amount of absorbent material in the respective region is calculated by determining the weight of absorbent material in this region and is dividing it by the total surface area of the region (hence, the average amount is taken). If the absorbent core has an uneven surface area, the projected surface area is taken, thus not taken the unevenness into account. In one embodiment, every area of the absorbent core back waist region 68 comprises not more than 0.01 gram of absorbent material per $cm^2$. Also, every area of the absorbent core front waist region 72 may comprise at least 0.03 gram of absorbent material per $cm^2$, or at least 0.04 grams per $cm^2$, and every area of the absorbent core crotch region 70 may comprise at least 0.04 gram of absorbent material per $cm^2$, or at least 0.05 gram per $cm^2$. In various embodiments, the absorbent material can comprise at least 90 weight-% of particulate absorbent polymer material, at least 95 weight-%, or even 100 weight-%.

In various embodiments, the relatively small amount of absorbent material 60 in the absorbent core back waist region 68 may make the disposable diaper more prone to a lack of opacity, thus, the problem of the present disclosure is especially pronounced in such embodiments. On the other hand, reduced amounts of absorbent material 60 may result in improved breathability, which improves the overall comfort of the disposable diaper 20.

The optional acquisition system 50 may comprise a single layer or multiple layers, such as an upper acquisition layer 52 facing towards the wearer and a lower acquisition 54 layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 28 can absorb the liquid.

In a certain embodiment, the acquisition system 50 may comprise chemically cross-linked cellulose fibers. Such cross-linked cellulose fibers may have desirable absorbency properties. Exemplary chemically cross-linked cellulose fibers are disclosed in U.S. Pat. No. 5,137,537. In certain embodiments, the chemically cross-linked cellulose fibers are cross-linked with between 0.5 mole % and 10.0 mole % of a $C_2$ to $C_9$ polycarboxylic cross-linking agent or between 1.5 mole % and about 6.0 mole % of a $C_2$ to $C_9$ polycarboxylic cross-linking agent based on glucose unit. Citric acid and polyacrylic acid are exemplary cross-linking agents.

In one embodiment, the lower acquisition layer 54 may consist of or may comprise a non-woven, which may be hydrophilic. Further, according to a certain embodiment, the lower acquisition layer 54 may comprise the chemically cross-linked cellulose fibers, which may or may not form part of a nonwoven material. Further, according to an embodiment, the lower acquisition layer 54 may comprise the chemically cross-linked cellulose fibers mixed with other fibers such as natural or synthetic polymeric fibers.

One way to reduce the bulk of disposable diapers is to optimize the distribution of the absorbent material in order to provide the absorbent material only in those regions, where it is really needed to absorb liquid. Thus, in those areas, which, in use, are hardly reached by any liquid at all, only a very small amount of absorbent material needs to be provided or even no absorbent material at all. By optimizing the distribution, the overall amount of absorbent material provided in disposable diapers can often be reduced, leading to reduced manufacturing cost.

It has been found, that absorbent material provided towards the back waist edge of disposable diapers is typically used to a low degree or even not used at all. Thus, the present disclosure refers to disposable diapers which have reduced amounts of absorbent materials provided in the back waist region.

Another way to reduce bulk and manufacturing cost of disposable diapers is the use of materials, such as films or nonwoven webs, with relatively low basis weight. However, as the basis weight of films and nonwoven webs is more and more reduced, these materials typically become more translucent. Increased translucency is especially apparent in those parts of disposable absorbent articles, where only very few materials are overlaying each other or where even only one layer of material is used. In today's disposable diapers, regions with few layers of material are typically the front and back ear panels.

Reducing the amount of absorbent material towards the back waist region of the disposable diaper may result in increased translucency in this area, as due to the removal of absorbent material, the back waist region typically only comprises nonwoven webs or films, typically comprised by the topsheet and backsheet of the disposable diaper. Low basis weight backsheet and topsheet materials providing relatively poor opacity have hitherto not been considered problematic as the absorbent material disposed between the topsheet and backsheet has helped to avoid any see-through.

However, despite leading to reduced bulk, it has now been found that the removal of absorbent material in the back waist region is not easily accepted by consumers, because many consumers associate the translucent area in the back waist region with insufficient absorbency and thus, low performance and an increased risk of leakage. Furthermore, see-through is assumed to give the disposable diaper a cheap, low-quality appearance.

The inventors have thus sought to reduce see-through in the chassis back waist region of the disposable diaper. The present disclosure provides a combination of a backsheet which has a relatively high percentage of printed surface area (i.e. a relatively high percentage of ink coverage), especially in the chassis back waist region of the disposable diaper. According to the present disclosure, the backsheet has a printed surface area of at least 14% in the chassis back waist region, or at least 20%, or even at least 25%. In certain embodiments, the chassis back waist region may even have a printed surface area of at least 50%, or at least 75%.

The printed surface area may be provided with any conventional printing method, such as flexo print or roto gravure printing. In various embodiments of the present disclosure, the printed area can be provided by using a coloured ink such as pink, violet, green, purple, blue or yellow, or a combination of different coloured inks. However, the specific color is not important for the present disclosure, as long as the printed surface area can be recognized with the naked eye.

Typically, an ink composition comprises a coloring agent, a binder polymer, a solvent and other additives. The coloring agent such as a pigment is dispersed in a binder polymer dissolved in a solvent. The ink composition forms an ink film on the substrate web which in turn consists of several sub-layers of resin mixed with a coloring agent.

The coloring agent may be generally termed as pigment which refers to a insoluble color matter used in finely dispersed forms. The pigments may be dyes, organic pigments or inorganic pigments. Exemplary organic pigments may include: C.I. Pigment Yellow 1, C.I. Pigment Yellow 3, C.I. Pigment Yellow 13, C.I. Pigment Red 5, C.I. Pigment Red 7, C.I. Pigment Red 12, C.I. Pigment Red 112, C.I. Pigment Red 122, C.I. Pigment Blue 1, C.I. Pigment Blue 2, C.I. Pigment Blue 16, C.I. Vat Blue 4, C.I. Vat Blue 6, or Carbon black. Exemplary inorganic pigments may include: carbon black (e.g., Pigment Black 7), iron oxides, ferric oxide black (e.g., Pigment Black 11), chromium oxide, or ferric ammonium ferrocyanide. Exemplary dyes may include: Solvent Yellow 14, Dispersed Yellow 23, Metanil Yellow, Solvent Red 111, Dispersed Violet 1, Solvent Blue 56, Solvent Orange 3, Solvent Green 4, Acid Red 52, Basic Red 1, Solvent Orange 63, or Jet Black.

Compared to a tinted backsheet, i.e. a backsheet, where the material per se is colored (e.g. by adding colored pigments when manufacturing the nonwoven webs or film layers making up the backsheet), a printed backsheet offers greater freedom and flexibility on design. Moreover, the materials have to be tinted upon manufacturing. As backsheet materials, such as film or nonwoven webs, are not always produced by the disposable diaper manufacturer but often are purchased from suppliers, any change in the tinted backsheet (such as color change or change in color intensity) has to be done in co-operation with the supplier. Especially if the backsheet material is provided by several supplier, a desired change for the tinted backsheet has to be done for several suppliers, ensuring that all suppliers deliver similar quality and color. This procedure is relatively complex and time demanding. Contrary thereto, print can be provided relatively easily on the backsheet material by the disposable diaper manufacturer during making of the diaper.

The ink used to provide the printed surface area of the present disclosure is non-white. In one embodiment of the present disclosure, the backsheet has a multi-colored printed surface area. Such a multi-colored printed surface area is regarded as being especially beneficial for addressing the problem of see-through, as the consumer will rather focus on the print and thus more readily tends to disregard any non-printed surface area. The print may be provided on any surface of the backsheet, i.e. the print may be provided on the body-facing surface (the surface facing towards the body of the wearer when the article is worn), or the print may be provided on the garment-facing surface (the surface facing towards the garment of the wearer when the article is worn). The multi-colored print may consist of two, three or more different colors.

In one embodiment of the present disclosure, the backsheet comprises a white nonwoven layer and a white film layer, wherein the printed surface area is provided either on the nonwoven layer, on the film layer or on both, the nonwoven layer and the film layer. In use, the film layer is facing towards the body while the nonwoven layer is facing towards the garment of the wearer.

In various embodiments of the present disclosure, the print is provided on the garment-facing surface of the film layer, as the print will be protected from abrasion (during use of the diaper) by the overlaying nonwoven layer. However, the nonwoven layer can have a relatively low basis weight which ensures that the print provided on the film layer remains visible when seen through the nonwoven layer. In various embodiments of the present disclosure, the nonwoven layer comprised by the backsheet can have a basis weight from 10 to 30 g/m$^2$, from 13 g/m$^2$ to 30 g/m$^2$, or even 15 g/m$^2$ to 25 g/m$^2$.

Alternatively, the print may also be provided on the nonwoven layer comprised by the backsheet. In such embodiments the print can be provided on the body-facing surface of the nonwoven layer. Thus, it can be ensured that that the print is not abraded in use. As the ink needed for an abrasion resistant print may be relatively expensive, the provision of the print on the body-facing surface can also contribute to reduced manufacturing cost.

Also, the printed surface area may not be a continuous area but a discontinuous area. Thus, the printed surface area in the back waist region is provided as an assembly of multiple smaller printed sub-surface areas. As used herein, the term "printed surface area" refers to the total amount of all printed surface areas in the respective region of the backhseet. It has been found that a discontinuous printed surface area allows reducing the amount of ink needed to ensure sufficient reduction of see-trough. In various embodiments of the present disclosure, at least 30% of the printed surface area, at least 50%, or even more 100% of the printed surface area can be provided in the form of a discontinuous pattern, wherein none of the discontinuous pattern elements has an area of more than 1 $mm^2$.

The topsheet of the present disclosure has an opacity of at least 15%, at least 17%, at least 18%, or even at least 20 according to the test method provided herein. In one embodiment, the topsheet is made of a nonwoven web, such as a polyolefin, such as polyethylene, polypropylene or mixtures thereof. Also, the nonwoven topsheet can be a multilayer nonwoven web. The nonwoven web can be manufactured by all well-known manufacturing techniques, such as spunbonding, meltblowing or carding. In one embodiment, the topsheet is a spunbonded nonwoven web, such as a dual layer spunbond (SS) or a nonwoven web comprising more than two layers, such as a spunbonded nonwoven with three layers (SSS). In an alternative embodiment, the topsheet is made of a film. In still another embodiment, the topsheet is a laminate of a nonwoven web and a film.

In one embodiment, the opacity of the topsheet is homogeneous throughout the topsheet.

If the topsheet material comprises more than one layer of material, than the complete topsheet material, i.e. all layers, are subjected to the opacity test method described below.

In embodiments, wherein the topsheet comprises a nonwoven web, the topsheet may also have bonded areas. In a bonded area, the fibers comprised by the bonded area are molten—at least to a considerable degree—and are thus bonded to each other. The bonded areas can be provided by heat bonding or a combination of pressure and heat bonding. The percentage of the bonded area can vary, however the overall bonded area of the topsheet (i.e. the total amount of bonded area) can be from 10% to 25%, or even from 14% to 22%.

The bonded area can be provided as a pattern of individual bond points. The bond points can take any shape, such as circular, diamond shape or any other shape, and the individual bond points may have equal size or may have a variety of different sizes. In one embodiment, at least 75% of all bond points have an area of from 2 $mm^2$ to 5 $mm^2$, or from 3 $mm^2$ to 5 $mm^2$. Such relatively large bond points have been shown to communicate absorbency to consumers, thus further helping to avoid that consumers conceive the disposable diaper as low performing with regard to liquid absorbency. Alternatively, the bonded area can be provided in the form of lines. In a further embodiment, the bonded area is provided as a combination of bond points and bond lines. As used herein, a "bond line" refers to a bonded area, which has a length to width ratio of more than 2, wherein a "bond point" refers to a bonded area with a length to width ratio of 2 or less. It is believed that both embodiments, i.e. bond points and bond lines can help to channel liquid, which may reduce the risk of liquid run off from the topsheet, and thus may reduce the risk of leakage.

The bonded area may be distributed evenly over the topsheet. However, in one embodiment, the bonded area at the longitudinal periphery of the topsheet is higher compared to the bonded area in the center of topsheet. As used herein "longitudinal periphery of the topsheet" refers to one third of the topsheet area starting from the longitudinal edges of the topsheet and extending towards the longitudinal axis. Thus, there is a left side longitudinal periphery of the topsheet making up one third of the topsheet area, a right side longitudinal periphery of the topsheet making up another third of the topsheet area, and a center region making up the one third of the area in the center of the topsheet and crossing the longitudinal axis. Such embodiments are generally advantageous as the increased bonded area in the lateral areas can direct liquid which may otherwise run-off the topsheet, resulting in leakage, while the lower amount of bonded area in the central region ensures that the amount of topsheet available for liquid absorption is not unduly reduced. This is especially beneficial, as the fibers comprised by the bonded area are molten, which in turn can result in reduced absorbency in the bonded area.

The bonded area may not extend into those layers of the disposable diaper which are positioned below the topsheet, such as the one or more layers of the acquisition system or the absorbent core. From a manufacturing point of view, these embodiments are advantageous, as the topsheet can be provided to the disposable diaper manufacturing line in pre-bonded and ready for assembly form. As such it can be joined with the other components of the disposable diaper (e.g. the absorbent core, backsheet) without need for further modification of the topsheet material. Thus, no additional process step is required in the disposable diaper manufacturing process.

Alternatively or in addition to providing the topsheet comprising a nonwoven web with a bonded area, the topsheet can be provided with an embossed area. As used herein, the term "embossed" refers to a densification of the fibers comprised by the embossed area, while the fibers are not bonded to each other by melting them to each other. Embossing is typically achieved by applying pressure. The embossing process may include the application of heat as long as the temperature does not exceed the melting temperature of the fibers.

The percentage of the embossed area can vary, however the overall embossed area of the topsheet (i.e. the total amount of embossed area) can be from 15% to 35%, or from 20% to 30%.

The embossed area may be provided as a pattern of individual embossed points. The embossed points can take any shape, such as circular, diamond shape or any other shape. Also, the size of the embossed points can vary and the embossed points may have equal size or may have a variety of different sizes. In one embodiment, at least 75% of all embossed points have an area of from 5 $mm^2$ to 10 $mm^2$, or from 7 $mm^2$ to 10 $mm^2$. Alternatively, the embossed area can be provided in the form of lines. In a further embodiment, the embossed area is provides as a combination of embossed points and embossed lines. As used herein, an "embossed line" refers to an embossed area, which has a length to width ratio of more than 2, wherein "embossed point" refers to a embossed area with a length to width ratio of 2 or less. Both embodiments, i.e. embossed points and embossed lines can help to channel liquid, which may reduce the risk of liquid run off from the topsheet, and thus may reduce the risk of leakage.

In certain embodiments, determining the actual dimensions of an embossed area on the topsheet material itself may be difficult as the change over from non-embossed area to embossed area may be gradually and thus, determining the actual borders of the embossed area may be problematic. Therefore, for the present disclosure, the dimensions given herein for an embossed topsheet are generally determined by the dimensions of the equipment used to provide the embossed pattern to the topsheet. Thus, while the dimensions can be approximated on the topsheet material, the pattern provided on the embossing equipment has to be determined and are equated with the embossed area for the present disclosure. In embodiments, wherein the pattern used to provide the embossed area (such as the protrusions on an embossing roll) do not have straight side-walls, the largest dimensions (i.e. the largest dimension of the width of the protrusions, not the height of the protrusions, which determine the depth of the embossed pattern in the topsheet material) on the embossing equipment are considered to be the dimensions for the present disclosure.

The embossed points may be distributed evenly over the topsheet. However, in one embodiment, the embossed area at the longitudinal periphery of the topsheet is higher compared to the embossed area in the center region of topsheet. Such embodiments are generally advantageous as the increased embossed area in the lateral areas can channel and temporarily hold liquid, thus reducing the risk of liquid run off.

The embossed area does not extend into those layers of the disposable diaper which are positioned below the topsheet, such as the one or more layers of the acquisition system or the absorbent core.

In one embodiment of the present disclosure the topsheet comprises a combination of bonded and embossed areas. Also, in such embodiments, the bonded areas as well as the embossed areas may be distributed evenly.

To achieve the necessary degree of opacity, the topsheet may be tinted. Tinting can be facilitated to provide one or more colored pigments when the topsheet material is manufactured. For example, suitable pigments can be provided to the polyolefin out of which the fibers of a nonwoven web are made.

For a given material, opacity also typically increases with increased basis weight. In one embodiment of the present disclosure, the topsheet has a basis weight of from 10 g/m² to 40 g/m², or from 14 g/m² to 30 g/m², or even from 14 g/m² to 25 g/m².

Moreover, opacity of the topsheet can be increased by adding Titanium Dioxide ($TiO_2$), which is a non-colored (white) pigment which enhances the "whiteness" of the topsheet. Titanium dioxide is generally present in an amount less than about 5 weight percent and more typically in an amount of from 0.5 weight percent to 5 weight percent, or from 1 weight percent to 4 weight percent, or even from 2 weight percent to 4 weight percent.

The topsheet can be non-apertured, as apertures will increase the opacity of the topsheet. However, if the apertures have a sufficiently small size, the opacity may not be adversely affected to a degree, that makes such apertured topsheets non-applicable for the present disclosure. Thus, the present disclosure also comprises embodiments, wherein the topsheet is apertured and wherein the aperture size is less than 2 mm² per aperture, or less than 1.5 mm², or even less than 1 mm² per aperture. The overall open area of the topsheet can be less than 20%, or less than 15%, or even less than 10%.

The opacity of the topsheet can be modified by applying lotion onto the wearer facing surface of the topsheet. In one embodiment of the present disclosure, a lotion is thus provided on the wearer facing surface of the topsheet. The lotion may not decrease the opacity of the topsheet and, in various embodiments, the lotion can increase the opacity of the topsheet. In such embodiments, the opacity is determined with the lotion applied onto the topsheet. However, in another embodiment the topsheet is free of lotion applied onto either of its surfaces.

Opacity Test Method

Opacity is a measure of the capacity of a material to obscure the background behind it. The value for opacity is obtained by dividing the reflectance obtained with a black backing (RB) for the material, by the reflectance obtained for the same material with a white background (WB). This is called the contrast ratio (CR) method.

$$\% \text{ Opacity} = \frac{RB}{RW} \times 100$$

Using a Hunter Colorimeter set to XYZ color scale, opacity is defined as $$\% \text{ Opacity} = \frac{Y \text{ reading over black plate}}{Y \text{ reading over white plate}} \times 100$$

Sample Preparation

A specimen of suitable size (generally about 10 cm square) is cut for analysis. The specimen must be free of creases, wrinkles, tears and other obvious defects.

If the opacity of the material is affected by temperature and/or humidity, the specimens must be conditioned under standard TAPPI conditions (73° F. (22.8° C.); 50% RH) until equilibrium is reached, and measured under those conditions.

If the topsheet material is treated with one or more surfactants, the material used for the test is the surfactant-treated topsheet material.

Equipment

Hunter Labscan® XE available from Hunter Associates Laboratory, Inc., USA. The instrument is configured as follows:

Geometry 45°/0°

Color Scale XYZ

Illuminant D65

Observer 10°

The colorimeter is calibrated using the standard gloss black glass and gloss white tile supplied with the instrument according to the manufacturer's instructions.

Test Procedure

The specimen is placed on the white tile and inserted into the colorimeter according to the manufacturer's instructions. The machine direction of the specimen should be aligned front-to-back in the instrument. The Y reading is recorded to the nearest 0.1 unit. The procedure is repeated using the black standard plate instead of the white standard tile.

Ten specimens are measured and the opacity results averaged to obtain the % opacity value for the material.

$$\% \text{ Opacity} = \frac{\text{"}Y\text{" on black plate}}{\text{"}Y\text{" on white plate}} \times 100$$

Examples of Topsheet Materials

Example 1

Spunbonded nonwoven available from Fiberweb Sweden AB, Sweden. The nonwoven is made of polypropylene, two layers of spunbond (SS material), basis weight 15 g/m$^2$, white, thermal pattern bonded with oval bond points, each bond point having a size of 0.363 mm$^2$, total bonded area 18.1%, with bond points evenly distributed.

Example 2

Spunbonded nonwoven available from Tesalca, La Selva del Camp, Tarragona (Spain). The nonwoven is made of polypropylene, three layers of spunbond (SSS material), basis weight 15 g/m$^2$, white, thermal pattern bonded with oval bond points, each bond point having a size of 0.363 mm$^2$, total bonded area 18.1%, with bond points evenly distributed.

Example 3

Spunbonded nonwoven available from Fiberweb Sweden AB, Sweden. The nonwoven is made of polypropylene, two layers of spunbond (SS material), basis weight 15 g/m$^2$, color Pantone® 324EC, thermal pattern bonded with oval bond points, each bond point having a size of 0.363 mm$^2$, total bonded area 18.1%, with bond points evenly distributed.

Example 4

Spunbonded nonwoven available from Fiberweb Sweden AB, Sweden. The nonwoven is made of polypropylene, one layer of spunbond (S material), basis weight 15 g/m$^2$, white, thermal pattern bonded with round bond points, each bond point having a size of 4.0 mm$^2$, total bonded area 25.0%, with bond points evenly distributed.

Example 5

Spunbonded nonwoven available from Fiberweb Sweden AB, Sweden. The nonwoven is made of polypropylene, one layer of spunbond (S material), basis weight 18 g/m$^2$, white, thermal pattern bonded with round bond points, each bond point having a size of 4.0 mm$^2$, total bonded area 25.0%, with bond points evenly distributed.

Example 6

Spunbonded nonwoven available from Fiberweb Sweden AB, Sweden. The nonwoven is made of polypropylene, one layer of spunbond (S material), basis weight 25 g/m$^2$, white, thermal pattern bonded with round bond points, each bond point having a size of 4.0 mm$^2$, total bonded area 25.0%, with bond points evenly distributed.

Comparative Example 1

Spunbonded nonwoven available from Fiberweb Sweden AB, Sweden. The nonwoven is made of polypropylene, one layer of spunbond (S material), basis weight 12 g/m$^2$, color Pantone® 324EC, thermal pattern bonded with round bond points, each bond point having a size of 4.0 mm$^2$, total bonded area 25.0%, with bond points evenly distributed.

Comparative Example 2

Spunbonded nonwoven available from Fiberweb Sweden AB, Sweden. The nonwoven is made of polypropylene, one layer of spunbond (S material), basis weight 12 g/m$^2$, white, thermal pattern bonded with round bond points, each bond point having a size of 4.0 mm$^2$, total bonded area 25.0%, with bond points evenly distributed.

| Example | Opacity [%] |
|---|---|
| 1 | 19.14 |
| 2 | 19.46 |
| 3 | 21.45 |
| 4 | 17.29 |
| 5 | 19.13 |
| 6 | 23.22 |
| Comparative 1 | 13.8 |
| Comparative 2 | 14.41 |

The opacity data show how opacity can be adjusted and changed by choosing nonwoven webs having varying basis weight, color, thermal bonding pattern, or different number of layers comprised by the nonwoven.

By choosing an appropriate topsheet material, incorporating it into a disposable diaper together with a backsheet having an appropriate percentage of printed surface area as well as in combination with a relatively short absorbent core, disposable diapers can be made according to claim 1, which have a sufficiently low degree of see-through in the chassis back waist region (where no absorbent core is positioned between the topsheet and backsheet material).

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper comprising a chassis, the chassis comprising a topsheet and a backsheet, the disposable diaper further comprising an absorbent core disposed between the topsheet and backsheet, wherein the chassis has a longitudinal dimension and a chassis back waist region, a chassis back waist edge, a chassis front waist region and a chassis crotch region, the chassis back waist region making up about 25% of the longitudinal dimension of the chassis beginning at the chassis back waist edge and extending towards the chassis crotch region, wherein the absorbent core has a longitudinal dimension co-extending with the longitudinal dimension of the chassis, the absorbent core having an absorbent core back waist region, an absorbent core front waist region and an absorbent core crotch region, wherein the absorbent core further has an absorbent core back waist edge, the absorbent core back waist edge being longitudinally offset by at least 10 percent from the chassis back waist edge, the 10% offset being based on the longitudinal dimension of the chassis;

wherein the absorbent core back waist region makes up about 25% of the longitudinal dimension of the absorbent core region and comprises about $0.01 \text{ g/cm}^2$ or less of absorbent material;

wherein the absorbent core front waist region makes up about 25% of the longitudinal dimension of the absorbent core region and comprises about $0.03 \text{ g/cm}^2$ or more of absorbent material;

wherein the absorbent core crotch region makes up about 25% of the longitudinal dimension of the absorbent core region and comprises about $0.04 \text{ g/cm}^2$ or more of absorbent material;

wherein the backsheet comprises a film layer and a nonwoven layer, the nonwoven layer having a basis weight from about $10 \text{ g/m}^2$ to about $30 \text{ g/m}^2$, and the backsheet has a percentage of printed surface area of about 50% or more, in the chassis back waist region; and wherein the topsheet has an opacity of at least 15%.

2. The disposable diaper of claim 1, wherein the chassis back waist edge comprises the back waist edge of the topsheet and the back waist edge of the backsheet.

3. The disposable diaper of claim 1, wherein the backsheet comprises a film layer and a nonwoven layer, the print being provided on the film layer.

4. The disposable diaper of claim 1, wherein the backsheet comprises a film layer and a nonwoven layer, the print being provided on the nonwoven layer.

5. The disposable diaper of claim 1, wherein the backsheet comprises a film layer and a nonwoven layer, the print being provided on the film layer and the nonwoven layer, wherein the printed surface area of the backsheet is determined when the film layer and the nonwoven layer are overlaying each other.

6. The disposable diaper of claim 3, wherein the film layer and the nonwoven layer are coextensive.

7. The disposable diaper of claim 1, wherein the absorbent core comprises a first and a second nonwoven web and absorbent material disposed between the first and second nonwoven webs.

8. The disposable diaper of claim 1, wherein the absorbent core comprises a nonwoven web, which envelops the absorbent material.

9. The disposable diaper of claim 1, wherein the absorbent core back waist region makes up 25% of the longitudinal dimension of the absorbent core beginning at the absorbent core back waist edge and extending towards the absorbent core crotch region, and wherein the absorbent core back waist region comprises not more than 0.01 gram of absorbent material per $cm^2$ of the absorbent core.

10. The disposable diaper of claim 1, wherein the absorbent material comprises at least 95% of particulate absorbent polymer material.

11. The disposable diaper of claim 1, wherein the opacity of the topsheet is homogeneous throughout the topsheet.

12. The disposable diaper of claim 1, wherein the topsheet comprises a nonwoven web.

13. The disposable diaper of claim 1, wherein the topsheet is tinted.

14. The disposable diaper of claim 1, wherein the topsheet comprises $TiO_2$.

15. The disposable diaper of claim 1, wherein the topsheet is bonded.

16. The disposable diaper of claim 1, wherein the topsheet is embossed, and wherein the absorbent core is non-embossed.

17. The disposable diaper of claim 1, the disposable diaper further comprising an acquisition system positioned between the absorbent core and the topsheet and wherein the acquisition system has a longitudinal dimension less or equal to the longitudinal dimension of the absorbent core, wherein the back waist edge of the acquisition system does not extend beyond the absorbent core back waist edge towards the chassis back waist edge.

18. The disposable diaper of claim 1, the disposable diaper further comprising an acquisition system positioned between the absorbent core and the topsheet, wherein the topsheet is embossed and wherein the acquisition system and the absorbent core are non-embossed.

* * * * *

UNITED STATES PATENT AND TRADEMARK OFFICE
CERTIFICATE OF CORRECTION

PATENT NO. : 9,000,254 B2  
APPLICATION NO. : 13/168548  
DATED : April 7, 2015  
INVENTOR(S) : McGregor et al.

Page 1 of 1

It is certified that error appears in the above-identified patent and that said Letters Patent is hereby corrected as shown below:

Claims

Claim 1, column 17, line 20, delete, "25%" and insert --50%--.

Signed and Sealed this  
Fifteenth Day of September, 2015

Michelle K. Lee  
*Director of the United States Patent and Trademark Office*